US00PP26315P3

(12) United States Plant Patent
Bradford et al.

(10) Patent No.: US PP26,315 P3
(45) Date of Patent: Jan. 19, 2016

(54) CHERRY TREE NAMED 'EL CAPITAN'

(50) Latin Name: *Prunus avium*
Varietal Denomination: El Capitan

(71) Applicants: Lowell Glen Bradford, Le Grand, CA (US); Jon Michael Quisenberry, Merced, CA (US)

(72) Inventors: Lowell Glen Bradford, Le Grand, CA (US); Jon Michael Quisenberry, Merced, CA (US)

( * ) Notice: Subject to any disclaimer, the term of this patent is extended or adjusted under 35 U.S.C. 154(b) by 239 days.

(21) Appl. No.: 13/998,852

(22) Filed: Dec. 16, 2013

(65) Prior Publication Data

US 2015/0173270 P1 Jun. 18, 2015

(51) Int. Cl.
*A01H 5/08* (2006.01)

(52) U.S. Cl.
USPC ..... Plt./181

(58) Field of Classification Search
USPC ..... Plt./181, 183
See application file for complete search history.

(56) References Cited

U.S. PATENT DOCUMENTS

PP15,512 P3 2/2005 Bradford

*Primary Examiner* — Susan McCormick Ewoldt
*Assistant Examiner* — Karen Redden

(57) ABSTRACT

The present invention relates to a cherry tree, *Prunus avium*, and more particularly to a new and distinct variety broadly characterized by a medium size, moderately vigorous, hardy, self unfruitful, productive and regular bearing tree. The fruit matures under the ecological conditions described in mid May, with first picking on May 17, 2013. The fruit is uniformly medium to large in size, very sweet in flavor, somewhat oblate in shape, clingstone in type, very firm in texture, red to pink in flesh color, and very dark red in skin color, and it has a short but strongly attached stem.

1 Drawing Sheet

Botanical classification: *Prunus avium.*
Varietal denomination: 'EL CAPITAN'.

BACKGROUND OF THE VARIETY

In a continuing effort to improve the quality of shipping fruits, we, the inventors, typically hybridize a large number of peach, nectarine, plum, apricot, and cherry seedlings each year. We also grow a smaller number of open pollinated seeds of each of these fruits, usually to capture recessive traits. The present invention relates to a new and distinct variety of cherry tree, which has been denominated varietally as 'El Capitan'.

During a typical blooming season we isolate as seed parents individual cherry trees by covering them with screen houses. A hive of bees is placed inside each such house, and bouquets to provide pollen from different cherry trees are placed in buckets near the trees approximately every two days for the duration of the bloom. During 2004 one such house containing 'Glenrock' (U.S. Plant Pat. No. 15,512) cherry tree was crossed by us in this manner. To pollinate this cherry, we selected bouquets from several sources of cherry trees without keeping specific written details. Upon reaching maturity the fruit from this cherry tree was harvested and the seeds were removed, cracked, stratified and germinated as a group with the label "Glenrock House". They were grown as seedlings on their own root in our greenhouse and upon reaching dormancy transplanted to a cultivated area of our experimental orchard located near Le Grand, Calif. in Merced County (San Joaquin Valley). During the summer of 2008 the claimed variety was selected by us as a single plant from the group of seedlings described above. Subsequent to origination of the present variety of cherry tree, we asexually reproduced it by budding and grafting in the experimental orchard described above, and such reproduction of plant and fruit characteristics were true to the original plant in all respects. The reproduction of the variety included the use of 'Colt' (unpatented) rootstock, upon which the present variety was compatible and true to type.

The present variety is most similar to its seed parent, 'Glenrock' (U.S. Plant Pat. No. 15,512) cherry, by being self unfruitful, by having reniform glands, and by producing fruit that is dark red in skin color, firm, sweet, and fairly crack resistant, but is distinguished therefrom by blooming about seven days later, and by producing cherries that are slightly larger, that ripen about six days later, and that have a shorter stem.

SUMMARY OF VARIETY

In summary, the present variety is characterized by a medium size, moderately vigorous, hardy, self unfruitful, productive and regular bearing tree. The fruit matures under the ecological conditions described in mid May, with first picking on May 17, 2013. The fruit is uniformly medium to large in size, very sweet in flavor, somewhat oblate in shape, clingstone in type, very firm in texture, red to pink in flesh color, and very dark red in skin color, and it has a short but strongly attached stem.

DRAWING

The accompanying photograph displays four fruits with the stems attached, two whole fruits detached from the stems to exhibit the skin color and form, two half fruits sectioned to reveal the flesh and fibers, an individual stone, two insets depicting flowers and buds, a typical tip shoot, and several leaves, all typical of the subject variety.

POMOLOGICAL CHARACTERISTICS

Referring now more specifically to the pomological characteristics of this new and distinct variety of cherry tree, the following has been observed under the ecological conditions prevailing near Le Grand, Merced County (San Joaquin Valley), Calif., and was developed at the state of firm ripe on May 21, 2013, on the original tree during its ninth growing season. All major color code designations are by reference to the Inter-Society Color Council, National Bureau of Standards. Common color names are also used occasionally.

PARENTAGE

Seed parent: 'Glenrock' cherry (U.S. Plant Pat. No. 15,512).
Pollen parent: Unknown.

TREE

Size: Medium, maintained to a height of 8' [2.44 m.] and a spread of 7' [2.13 m.] after nine growing seasons utilizing typical pruning.
Vigor: Medium vigor, responding typically to irrigation and fertilization. The plant should be grown on a standard commercial rootstock for production purposes.
Growth: Upright and dense.
Form: Vase formed.
Hardiness: Hardy with respect to central California winters.
Heat tolerance: Observed to perform adequately in typical central California climatic conditions, which typically include extended periods of heat.
Drought tolerance: Variety is developed for commercial orchards and requires regular irrigation.
Production: Productive.
Fertility: Self-sterile, must be cross pollinated by another mid seasonal blooming cherry variety, such as 'Bing' (unpatented).
Bearing: Regular bearer, with no crop failures observed.
Trunk:
- *Size.*—Medium, reaching a maximum diameter of 4" [101.6 mm.] after the ninth growing season.
- *Texture.*—Medium shaggy.
- *Bark color.*—A Light brownish gray [63. l.brGy] and Brownish gray [64. brGy] variegation.
- *Lenticels.*—Approximate Number Per Square Inch: 6. Color: Strong yellowish brown [74. s.yBr]. Average Size: 3/16" [4.8 mm.] to 5/8" [15.9 mm.]. Shape: Elongated, eye-shaped.

Branches:
- *Size.*—Diameter of main scaffold measured 12" above the crotch is 2¾" [69.9 mm.]. Diameter of first limb measured 12" above first fork is 1" [25.4 mm.].
- *Texture.*—Smooth on first and second year wood, increasing roughness with age.
- *Color.*—1st Year Wood topside: Grayish red [19. gy.R]. 1st Year Wood underside: Brilliant yellow green [116. brill.YG]. 2nd Year Wood: A Light grayish brown [60. l.gy.Br] and Grayish brown [61. gy.Br] variegation with Moderate brown [58. m.Br] crevices present.
- *Lenticels.*—Number Per Square Inch: About 15 on second year wood. Color: Brownish orange [54. brO]. Size: 1/64" [0.4 mm.] to 1/16" [1.6 mm.]. Shape: Eye-shaped, elongated.

Leaves:
- *Size.*—Large. Average Length: 6½" [165.1 mm.]. Average Width: 2⅜" [60.3 mm.].
- *Arrangement.*—Alternate.
- *Thickness.*—Medium.
- *Form.*—Elliptical.
- *Apex.*—Acuminate.
- *Base.*—Rounded.
- *Surface.*—Smooth.
- *Color.*—Dorsal Surface: Moderate olive green [125. m.OlG]. Ventral Surface: Moderate yellow green [120. m.YG].
- *Margin.*—Finely serrate.
- *Venation.*—Pinnately net veined.
- *Vein color.*—Brilliant yellow green [116. brill.YG].
- *Petiole.*—Average Length: 1¼" [31.8 mm.]. Average Thickness: ⅛" [3.2 mm.]. Color: Grayish red [19. gy.R] on the topside and Moderate yellow green [120. m.YG] underneath.
- *Stipules.*—Number: 2 to 6 per leaf at development stage. Average Length: ¼" [6.4 mm.]. Color: Moderate yellow green [120. m.YG] becoming Moderate olive green [125. m.OlG] with age.
- *Glands.*—Number: Mostly 2 per leaf. Position: Slightly alternate on the petiole just below the leaf blade. Size: Medium. Form: Reniform. Color: Strong yellow green [117. s.YG] becoming Dark olive green [126. d.OlG] with age.
- *Leaf buds.*—Pointed, medium.

Flower buds:
- *Hardiness.*—Hardy, with respect to central California winters.
- *Diameter.*—Typically 5/16" [7.9 mm.] 3 days before bloom.
- *Length.*—Typically ⅝" [15.9 mm.] 3 days before bloom.
- *Form.*—Free.
- *Surface.*—Non-pubescent.
- *Tip color.*—White [263. white].

Flowers: Perfect, complete, perigynous, usually a single pistil, typically about twenty stamens, five sepals and petal locations alternately positioned.
- *Average flower diameter.*—1⅜" [34.9 mm.].
- *Number of petals.*—Usually five, very few have extra petals or fragments.
- *Petal shape.*—Circular to slightly oval.
- *Petal margin.*—Somewhat wavy with occasional serrations.
- *Average petal diameter.*—⅝" [15.9 mm.].
- *Average petal length.*—11/16" [17.5 mm.].
- *Petal apex.*—Rounded with a small notch on some.
- *Petal base.*—Cuneate to acuminate.
- *Petal color.*—White [263. white].
- *Anther color.*—Pale yellow [89. p.Y].
- *Stigma color.*—Brilliant greenish yellow [98. Brill.gY].
- *Sepal color.*—Deep reddish orange [36. deep rO] over Vivid greenish yellow [97. v.gY].
- *Sepal length.*—5/16" [7.9 mm.].
- *Sepal width.*—3/16" [4.8 mm.].
- *Average pistil length.*—⅝" [15.9 mm.].
- *Average stamen length.*—9/16" [14.3 mm.].
- *Fragrance.*—Moderate.
- *Pollen production.*—Moderate.
- *Bloom density.*—Heavy.

*Blooming period.*—Medium to late, four days before 'Bing' (unpatented).
*Onset of bloom.*—One percent on Mar. 18, 2013.
*Date of full bloom.*—Mar. 26, 2013.
*Duration of bloom.*—One to two weeks, dependent on ambient temperature.
*Number per cluster.*—Usually 2 to 10, 5 average.

FRUIT

Maturity when described: Firm ripe, May 21, 2013.
Date of first picking: May 17, 2013.
Date of last picking: May 25, 2013.
Size: Uniform, medium to large.
*Average diameter axially.*—15/16" [23.8 mm.].
*Average diameter across cheek plane.*—1⅛" [28.6 mm.].
*Average diameter across suture plane.*—⅞" [22.2 mm.].
*Typical weight.*—0.36 ounces [10.2 grams].
Form: Uniform, symmetrical, somewhat oblate, compressed axially and toward the suture.
*Cheek plane form.*—Elliptical.
*Suture plane form.*—Oval.
*Axial view form.*—Elliptical.
Suture: An inconspicuous line located in a shallow trough extending from the base to the pistol point.
Ventral surface: Rounded, lipped slightly on a few.
Lips: Mostly equal.
Cavity: Flaring, circular, suture showing on one side.
*Depth.*—3/16" [4.8 mm.].
*Breadth.*—9/16" [14.3 mm.].
Base: Somewhat truncate if viewed in the suture plane, cordate if viewed parallel to the suture.
Apex: Rounded.
Pistil point: A Light yellowish brown [76. l.yBr] inconspicuous dot.
Stem: Short.
*Average length.*—1⅛" [28.6 mm.].
*Average width.*—1/16" [1.6 mm.].
Stem attachment: Very strong.
Skin:
*Thickness.*—Medium.
*Surface.*—Smooth.
*Tenacity.*—Tenacious to the flesh.
*Astringency.*—Slight.
*Tendency to crack.*—None observed in dry seasons, fairly resistant to cracking in wet season.
*Color.*—A Very dark red [17. v.d.R] over a Dark red [16. d.R] background.
Flesh:
*Color.*—Deep pink [3. deep Pk] near the skin and Deep red [13. deep R] near the stone.
*Surface of pit cavity.*—Covered with Deep red [13. deep R] broken fibers when twisted away from the stone.
*Amygdalin.*—Moderate.
*Juice.*—Abundant, rich.
*Juice color.*—Dark red [16. d.R].
*Texture.*—Very firm, crisp, meaty.
*Fibers.*—Abundant, fine, tough.
*Ripens.*—Mostly even, slightly earlier at the apex.
*Flavor.*—A nice balance of acid and sugar, typically 22-26 brix.
*Aroma.*—Slight.
*Eating quality.*—Excellent.

STONE

Type: Clingstone.
Form: Oval.
Hilum: Narrow, oval.
Base: Rounded.
Apex: Rounded.
Sides: Equal.
Surface: Fairly smooth.
External color of stone: Light yellowish brown [76. l.yBr] when first removed.
Pit wall color when cracked: Light yellowish brown [76. l.yBr].
Cavity surface color: Moderate yellowish brown [77. m.yBr].
Average pit wall thickness: 3/64" [1.2 mm.].
Average width: ⅜" [9.5 mm.].
Average length: 7/16" [11.1 mm.].
Average breadth: ¼" [6.4 mm.].
Tendency to split: None observed in dry season.
Kernel:
*Form.*—Oval.
*Skin color.*—Yellowish white [92. yWhite] when first removed.
*Pellicle color.*—Grayish yellow [90. gy.Y].
*Apex tip color.*—Strong yellowish brown [74. s.yBr] when first removed.
*Taste.*—Bitter.
*Viable.*—Yes.
*Average width.*—3/16" [4.8 mm.].
*Average length.*—5/16" [7.9 mm.].
*Amygdalin.*—Abundant.

USE

Market: Fresh market and long distance shipping.
Keeping quality: Good, fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.
Other notes: Although the new variety of cherry tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of cherry tree, substantially as illustrated and described, that is most similar to its seed parent, 'Glenrock' (U.S. Plant Pat. No. 15,512) cherry, by being self unfruitful, by having reniform glands, and by producing fruit that is dark red in skin color, firm, sweet, and fairly crack resistant, but is distinguished therefrom by blooming about seven days later, and by producing cherries that are slightly larger, that ripen about six days later, and that have a shorter stem.

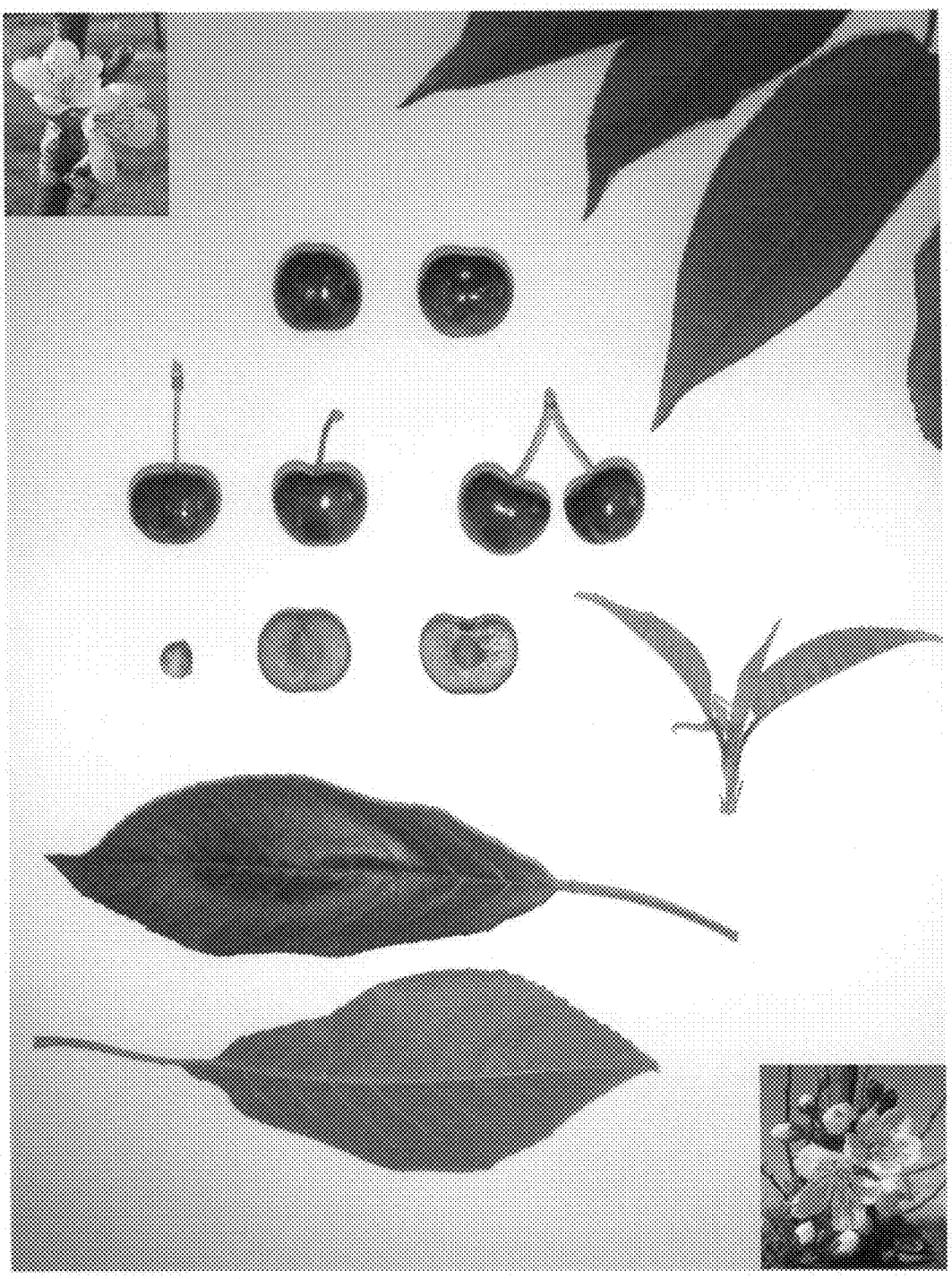

* * * * *